United States Patent [19]

Dondi et al.

[11] Patent Number: 5,624,682
[45] Date of Patent: Apr. 29, 1997

[54] PHARMACEUTICAL FORMULATIONS BASED ON A KETOPROFEN SOLUTION IN SOFT CAPSULES, AND PROCESSES FOR THEIR PREPARATION

[75] Inventors: Gilberto Dondi, Cusano Milanino; Paolo Scurati, Paderno Dugnano, both of Italy

[73] Assignee: Bayer S.p.A., Milan, Italy

[21] Appl. No.: 421,712

[22] Filed: Apr. 13, 1995

[30] Foreign Application Priority Data

Apr. 26, 1994 [IT] Italy ................... MI94A0801

[51] Int. Cl.$^6$ ................ A61K 9/48; A61K 9/66; A61K 31/54; A61K 31/44

[52] U.S. Cl. ................... 424/455; 424/451; 424/452; 514/226.5

[58] Field of Search ................... 424/451, 452, 424/455

[56] References Cited

U.S. PATENT DOCUMENTS 5,141,961  8/1992  Coapman.

Primary Examiner—Shep K. Rose
Attorney, Agent, or Firm—Sprung Horn Kramer & Woods

[57] ABSTRACT

The present invention relates to a stable pharmaceutical formulation which comprises ketoprofen, and in particular to a formulation which comprises ketoprofen in a carrier, such as, for example, polyethylene glycol.

6 Claims, No Drawings

PHARMACEUTICAL FORMULATIONS BASED ON A KETOPROFEN SOLUTION IN SOFT CAPSULES, AND PROCESSES FOR THEIR PREPARATION

The present invention relates to a stable pharmaceutical formulation which comprises ketoprofen, and in particular to a formulation which comprises ketoprofen in a carrier, such as, for example, polyethylene glycol.

This pharmaceutical formulation offers the possibility of making available a medicament having a very rapid therapeutic action, which is particularly beneficial for administration of an active compound having an analgesic action.

The present invention furthermore also relates to a process for the preparation of such pharmaceutical formulations.

It is known that ketoprofen, i.e. 2-(3-benzoylphenyl) propionic acid, is used extensively in medicine as an anti-inflammatory and analgesic agent. It is available in various drug forms for oral, topical and parenteral use and the like. However, there was a need to increase the rate of absorption of the forms for oral administration considerably, in order to accelerate the biological availability of the medicament to the maximum, to achieve a very rapid pharmacological action.

The object of the present invention is therefore to provide a drug form which is capable of guaranteeing rapid absorption, on the part of the organism, of the orally administered ketoprofen.

This object is achieved according to the present invention by the pharmaceutical formulation characterized in the main claim.

The expert knows several methods of incorporating an active compound into soft gelatin capsules, for example incorporation of the active compound into a dispersion in a fat-based carrier, if appropriate with the addition of surfactants.

However, it is known that it is often preferable to administer drugs as a solution in water or in another hydrophilic solvent, since the phase of dissolution of the drug in the digestive apparatus can thus be avoided. This is particularly desirable in the case of analgesics, since a rapid pharmacological action is a choice criterion. Another disadvantage of the use of fat-based carrier substances is that they form opaque capsules which do not have a pleasant appearance, and for this reason it is essential to employ pigments and/or dyestuffs in order to impart to the composition aesthetic features which help to improve acceptance on the part of the patients. It has thus been found that polyethylene glycols (PEG) having a molecular weight of between 200 and 600 are particularly suitable substances for formulation of ketoprofen solutions for incorporation into soft gelatin capsules. According to the present invention, ketoprofen is dissolved in a polyethylene glycol having a molecular weight of between 200 and 600 in a ketoprofen-:PEG ratio of between 1:8 and 1:2.

Another critical criterion within the present invention is the pH of the ketoprofen solution in the polyethylene glycol, in order to guarantee an appropriate stability of the pharmaceutical formulation and to improve its tolerability. The best results have been achieved for pH values of between 5 and 7. According to the present invention, these pH values can be achieved by means of addition of expedient neutralizing agents, such as, for example, colamine (ethanolamine), lysine, triethanolamine, methylglucamine and in general any appropriate amine of the type used for formulation of pharmaceutical compositions.

According to the invention, the preparation of pharmaceutical formulations based on ketoprofen in soft gelatin capsules is carried out in two stages. An appropriate amount of gelatin, glycerol and purified water are first dissolved by methods known to the expert, by heating these ingredients at a temperature of about 80° C. for 3 hours, while shaking constantly. After deaeration under reduced pressure, the solution thus prepared is stored at about 50° C. for preparation of soft capsules.

Thereafter, a therapeutically active amount of ketoprofen is dissolved in an appropriate amount of PEG, the pH is brought to a value of between 5 and 7 with a pharmaceutically tolerated base, where necessary, and the mixture is shaken until a transparent solution is achieved. If it should be regarded as beneficial, small amounts of sterile water, propylene glycol, glycerol, preservative or other additives such as are generally used for formulation of pharmaceutical compositions in the form of soft capsules can be added to this solution.

Finally, the solution according to the invention is encapsulated, methods and apparatuses such as are generally used for formulation of this specific pharmaceutical form being used.

The invention is illustrated in more detail by means of the following Examples. As soon as the basic principles for realization of the pharmaceutical formulations according to the present invention in the form of soft gelatin capsules are understood, the expert of pharmaceutical formulations will have no difficulty at all in adapting the process criteria to the particular needs without thereby distancing himself from the inventive idea.

EXAMPLE 1

Formulation of soft ketoprofen capsules of 25 mg each 5000 soft gelatin capsules, each of which contains 25 mg of ketoprofen, were formulated with the following ingredients:

| Gelatin per capsule | g 460.0 |
| --- | --- |
| Glycerol | g 140.0 |
| Purified water | g 330.0 |
| Ketoprofen | g 125.0 |
| PEG 600 | g 625.0 |
| Ethanolamine | g 28.1 |

The formulation of the gelatin shell used for preparation of the soft capsules is not in itself a part of the present invention, since this is already known. In general, these shells are formulated by companies which specialize in the production of soft gelatin capsules.

The formulation is explained below in broad outline with the sole purpose of providing a complete description of the invention. The gelatin is mixed in the abovementioned amount with glycerol and purified water in the amounts stated, the mixture being heated at 80° C. for 3 hours, with constant shaking. After deaeration under reduced pressure, the solution thus obtained is maintained at a temperature of 50° C. until the layer for the shell is prepared. As is known to the expert, other substances can be added to this solution where this is considered necessary, such as, for example, propylene glycol, sorbitol, preservative and dyestuffs. Thereafter, the ketoprofen is dissolved in PEG 600 with the addition of ethanolamine, in the abovementioned amounts, and the mixture is shaken until a transparent solution is obtained; in this manner, the constituents of the pharmaceutical formulation of the invention have a form appropriate for encapsulation. The individual capsules, each of which contains 25 mg of ketoprofen, are then formulated by encapsulating 156 mg of the solution described above in a manner known per se.

EXAMPLE 2

Formulation of soft capsules having in each case 50 mg of ketoprofen 2500 soft capsules which each contain 50 mg of ketoprofen were formulated in accordance with the description in Example 1, but using 312 mg of ketoprofen solution, instead of 156 mg.

EXAMPLE 3

In accordance with the process described in Example 1, 125 g of ketoprofen are dissolved in 625 g of PEG 400. The pH of the solution is established with 135 g of 50% strength DL-lysine, and 5000 soft capsules having in each case 25 mg of ketoprofen are formulated in accordance with Example 1.

EXAMPLE 4

In accordance with the process described in Example 1, 125 g of ketoprofen are dissolved in a mixture of 400 g of PEG 600 and 125 g of PEG 400. The pH of the solution is corrected with 27.9 g of ethanolamine, and soft capsules are formulated by encapsulating 156 mg of the solution thus prepared in each, in which case the dosage will be 25 mg of therapeutically acting substance per capsule, while 312 mg of the same solution must be encapsulated for formulation of capsules having in each case 50 mg of ketoprofen.

EXAMPLE 5

In accordance with the process described in Example 1, 125 g of ketoprofen are dissolved in a mixture of 600 g of PEG 400 and 25 g of glycerol. 28 g of ethanolamine are added and encapsulation is carried out in accordance with the conditions described in Example 1, corresponding to a dosage of 156 g or 312 g of the solution thus prepared.

We claim:

1. A pharmaceutical formulation for oral administration having an increased stability and bioavailability of an analgesic or antiflammatory agent, comprising a soft gelatin capsule which essentially contains a therapeutically active amount of ketoprofen dissolved in polyethylene glycol containing a neutralizing organic amine in amount to bring the pH of the solution to between 5 and 7.

2. A pharmaceutical formulation according to claim 1, wherein the polyethylene glycol has an average molecular weight of between 200 and 600.

3. A pharmaceutical formulation according to claim 1, wherein the ratio of ketoprofen to polyethylene glycol is between 1:8 and 1:2.

4. A pharmaceutical formulation according to claim 1, wherein the organic amine comprises at least one member selected from the group consisting of ethanolamine, lysine, triethanolamine and methylglucamine.

5. A pharmaceutical formulation according to claim 1, wherein the polyethylene glycol is a mixture of at least two polyethylene glycols each having an average molecular weight of between 200 and 600.

6. A pharmaceutical formulation according to claim 1, wherein the ratio of ketoprofen to polyethylene glycol is between 1:8 and 1:2, and the organic amine comprises at least one member selected from the group consisting of ethanolamine, lysine, triethanolamine and methylglucamine.

* * * * *